(12) United States Patent
Skoog et al.

(10) Patent No.: US 9,254,504 B2
(45) Date of Patent: Feb. 9, 2016

(54) ARRANGEMENT AND METHOD FOR SIMULATING CREPING OF TISSUE PAPER

(71) Applicant: Kemira Oyj, Helsinki (FI)

(72) Inventors: Henry Skoog, Roswell, GA (US); Pyry Hämäläinen, Karlstad (SE); Vladimir Grigoriev, Cologne (DE)

(73) Assignee: KEMIRA OYJ, Helsinki (FI)

( * ) Notice: Subject to any disclaimer, the term of this patent is extended or adjusted under 35 U.S.C. 154(b) by 132 days.

(21) Appl. No.: 14/162,824

(22) Filed: Jan. 24, 2014

(65) Prior Publication Data
US 2015/0209827 A1 Jul. 30, 2015

(51) Int. Cl.
| B05C 5/02 | (2006.01) |
| B05D 5/00 | (2006.01) |
| B05C 5/00 | (2006.01) |
| B31F 1/12 | (2006.01) |

(52) U.S. Cl.
CPC . *B05D 5/00* (2013.01); *B05C 5/004* (2013.01); *B31F 1/12* (2013.01); *B05C 5/001* (2013.01); *B05C 5/002* (2013.01); *B05D 2203/22* (2013.01)

(58) Field of Classification Search
None
See application file for complete search history.

(56) References Cited

U.S. PATENT DOCUMENTS

| 4,225,382 | A | * | 9/1980 | Kearney | D21F 1/0027 162/111 |
| 4,994,146 | A | | 2/1991 | Soerens | |
| 5,246,544 | A | | 9/1993 | Hollenberg et al. | |
| 5,611,890 | A | * | 3/1997 | Vinson | D21H 17/68 162/111 |
| 5,865,950 | A | * | 2/1999 | Vinson | B31F 1/12 162/112 |
| 6,176,972 | B1 | * | 1/2001 | Oriaran | D21F 11/006 162/111 |
| 6,454,901 | B1 | * | 9/2002 | Sekiya | B31F 1/14 162/111 |
| 7,744,722 | B1 | * | 6/2010 | Tucker | D21H 21/146 156/183 |
| 7,879,189 | B2 | * | 2/2011 | Dyer | A61K 8/0208 162/112 |
| 2003/0116259 | A1 | * | 6/2003 | Sayovitz | D04H 1/70 156/183 |
| 2005/0217814 | A1 | * | 10/2005 | Super | B31F 1/126 162/111 |
| 2007/0000631 | A1 | | 1/2007 | Grigoriev et al. | |
| 2008/0216977 | A1 | * | 9/2008 | Dyer | A47K 10/16 162/112 |

(Continued)

FOREIGN PATENT DOCUMENTS

| WO | WO0174581 | 10/2001 |
| WO | WO2013142244 | 9/2013 |

OTHER PUBLICATIONS

Ho, J., Hutton, B, Proctor, J. and Batchelor, W.: "Development of a tissue creping test rig", Chemeca 2007, IChemEA (2007), p. 1334-1340.

(Continued)

*Primary Examiner* — Dah-Wei D Yuan
*Assistant Examiner* — Jethro M Pence
(74) *Attorney, Agent, or Firm* — Thomas Horstemeyer. LLP

(57) ABSTRACT

The invention relates to an arrangement for simulating creping of tissue. The arrangement comprises a sled with a test surface, which sled is arranged to travel along a linear path; heating means for heating the test surface; a spray unit with at least one spray nozzle, the spray unit being arranged along the linear path of the sled and the at least one spray nozzle being arranged to spray a chemical on the test surface; a creping unit comprising a creping blade, the creping unit arranged along the linear path of the sled after the spray unit and the creping blade arranged to pass over the test surface when the sled passes the creping unit; and measurement means for measuring data related to force between the creping blade and the test surface. The invention relates also to a method for simulating creping of tissue.

7 Claims, 1 Drawing Sheet

(56) References Cited

U.S. PATENT DOCUMENTS

2012/0164206 A1* 6/2012 Soerens .................... B31F 1/14
 424/414
2012/0255694 A1* 10/2012 Druecke ................ D21H 17/29
 162/111
2013/0269892 A1* 10/2013 Hermans ................ A47K 10/16
 162/111

OTHER PUBLICATIONS

International Search Report of Apr. 7, 2015; Application No. PCT/FI2015/050038; European Patent Office, The Netherlands; 3 pages.

* cited by examiner

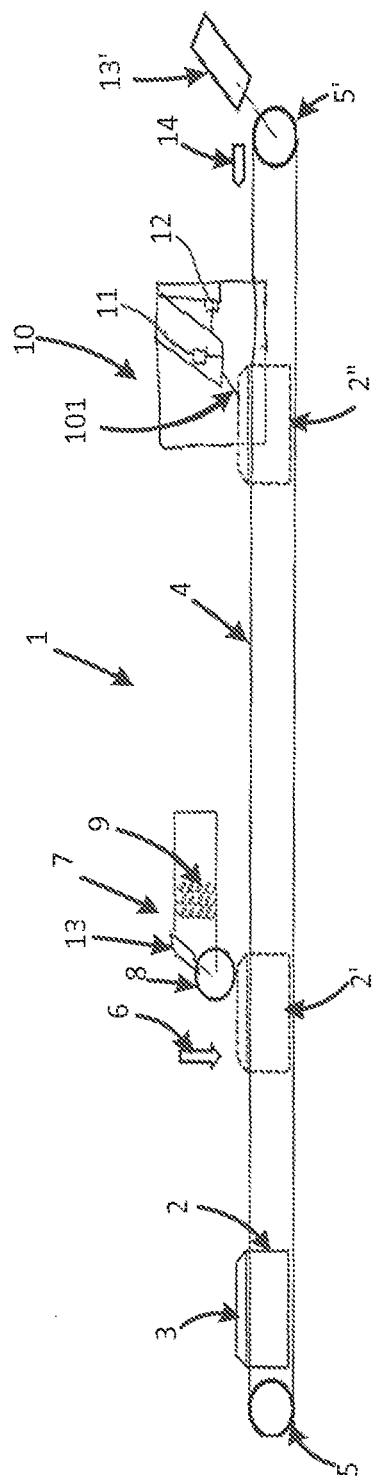

ARRANGEMENT AND METHOD FOR SIMULATING CREPING OF TISSUE PAPER

The invention relates to an arrangement and method for simulating creping of tissue paper according to the preambles of the enclosed independent claims.

Creping is one of the important processes on a tissue machine. The sheet is adhered to a Yankee cylinder surface where it is dried. The dried sheet is then peeled off the cylinder surface with a doctor blade, whereby microfolds are created in the sheet. These changes in the structure of the sheet influence greatly to the final sheet properties, such as softness and stretch. The creping process may often become a bottleneck in the production that decreases machine speed and efficiency. In order to improve the creping process various chemicals may be added to the surface of the Yankee cylinder. Possible chemicals are adhesives, release agents and modifiers. It is possible to add one or more of these chemicals to the surface of the Yankee cylinder for optimal creping performance at varying process situations.

One problem is the testing of the chemicals which are employed in the creping process. Quite naturally, testing of new chemicals or new different chemical combinations is preferably not made by using real production apparatus. Thus there is a need for test apparatuses with which different creping chemicals may be tested. One experimental rig for trialing new creping chemicals and determining their optimum conditions is presented by Ho, J., Hutton, B, Proctor, J. and Batchelor, W.: "Development of a tissue creping test rig", Chemeca 2007, IChemEA (2007), p. 1334-1340. However, the proposed solution does not provide an environment which is representative to real process conditions. For example, the speed of the process is much lower than in real life.

An object of the present invention is to minimise or even completely eliminate the problems existing in the prior art.

One object of the present invention is to provide an arrangement and method for simulating creping of tissue in as real process conditions as possible.

Another object of the present invention is to provide an arrangement and method for testing different process chemicals in creping of tissue.

These objects are attained with a method and an arrangement having the characteristics presented below in the characterizing parts of the independent claims.

Typical arrangement according to the present invention for simulating creping of tissue, the arrangement comprising a sled with a test surface, which sled is arranged to travel along a linear path;

heating means for heating the test surface;

a spray unit with at least one spray nozzle, the spray unit arranged along the linear path of the sled, and the at least one spray nozzle arranged to spray a chemical on the test surface;

a creping unit comprising a creping blade, the creping unit arranged along the linear path of the sled after the spray unit and the creping blade arranged to pass over the test surface when the sled passes the creping unit; and measurement means for measuring data related to force between the creping blade and the test surface.

Typical method according to the present invention for simulating creping of tissue, the method comprising heating a test surface to a predetermined temperature;

transferring the test surface along a linear path;

spraying a chemical to the test surface;

arranging a creping blade to pass over the test surface after the spraying of the chemical; and measuring and collecting data related to force between the creping blade and the test surface.

All the described embodiments and advantages apply both for the arrangement and the method according to the present invention, when applicable, even if not always explicitly stated so.

Now it has been surprisingly found out that the creping process, its conditions and relevant forces between the creping blade and the Yankee cylinder can be effectively simulated by applying the chemical to be tested onto a heated test surface which is transferred along a linear path so that it passes a creping blade. Data related to force between the creping blade and the test surface, such as orthogonal force, is measured and collected, which gives good and reliable estimate of forces prevailing in real life process conditions. The linear path of the test surface provides a possibility to use high test speeds, which better corresponds to the industrial process speeds. The arrangement of the present invention is designed to closely approximate various production variables, such as temperature of the Yankee cylinder surface; concentration, formulation and time-to-dry of the applied chemical; as well as different creping blade parameters. All this provides new and exciting possibilities for testing of different chemicals and chemical compositions for creping of tissue.

According to one embodiment of the invention the test surface is a part of a test plate, which is detachably arranged to the sled transferred along the linear path. The test surface, and optionally also the test plate, can be made of any material which corresponds to a Yankee cylinder material used in industrial production of tissue. The test surface may be made of cast iron, stainless steel or a metallized coating on a cast iron plate. According to one embodiment the test surface is slightly sloping in the leading edge and/or rear edge, seen in the direction of the transfer. The height difference between the leading/rear edge of the surface and the middle part of the surface may be 1-4 mm, preferably approximately 2 mm. The slightly sloping form of the test surface ensures a smooth travel of the creping blade over the test surface.

The test surface is heated by using heating means. According to one embodiment of the invention the heating means comprises a heating element, which is arranged to the sled. Typically the test surface is heated to a temperature of at the most 135° C., preferably 80-130° C., more preferably 90-115° C., even more preferably 95-110° C. The temperature of the test surface is preferably adjustable. Adjustment step may be, for example, 0.1° C. The temperature of the test surface may be controlled by using a temperature sensor. In one embodiment, a stationary infrared (IR) temperature sensor may be arranged over the test surface at the start position of the test surface. If the temperature of the test surface exceeds a predetermined threshold value, the heating is interrupted, e.g. by discontinuing power supply to the heating means. The predetermined threshold value can be chosen on basis of the process to be simulated. For example, the heating can be interrupted when the test surface temperature exceeds 120° C.

An isolation layer may be arranged between the test plate with the test surface and the heating means, in such a manner that a direct contact with the test plate and the heating means is avoided. The isolation layer may be made of, for example, Teflon or silicon cloth.

The test surface is arranged to a sled, which is moved along a linear, preferably horizontal, path. The test plate with the test surface may be fastened to the sled by using any suitable fastening means, such as angle brackets, bolts, screws, pins, or the like. Preferably the sled comprises a stopper plate in the in the leading end and/or rear end of the sledge, seen in the direction of transfer, in order to keep the test surface securely positioned on the sled. The sled may comprise transfer means, such as adjustable V-bearings with eccentric shafts. These transfer means can be fitted to the grooves of the guide rail. The sled may optionally comprise a lubricating box between the bearings for applying grease or oil on the grooves of the rail. The sled may be operated by sled drive means, such as a servomotor or the like, and a timing belt or the like.

Speed of the sled along the linear path may be 5-35 m/s, preferably 5-30 m/s, more preferably 10-25 m/s, when it passes the creping blade. This means that the test surface is transferred with a speed of 5-35 m/s, preferably 5-30 m/s, more preferably 10-25 m/s, while the creping blade passes over the test surface. According to one embodiment the speed of the sled, and the test surface, may be in the range 6-12 m/s. The sled starts from a determined zero position in the first end of the guide rail and is accelerated to a predetermined first speed before it passes the spray unit. The acceleration of the sled may be at the maximum of 30 m/s$^2$, preferably 5-30 m/s$^2$, more preferably 10-30 m/s$^2$, and its deceleration at the maximum of 34 m/s$^2$, preferably 5-34 m/s$^2$, more preferably 15-34 m/s$^2$. According to one embodiment the drying speed of the chemical(s) applied at the spray station can be influenced and selected by selecting the speed of the sled and/or the temperature of the test surface. In this manner various different process conditions of commercial production operation can be successfully simulated.

The spray unit comprises at least one spray nozzle, optionally a plurality of spray nozzles. The spray nozzles are arranged to spray at least one chemical or chemical mixture on the heated test surface when the sled with the test surface passes the spray unit. The applied chemical, such as adhesive, begins to dry on the heated test surface, thus corresponding to the situation in industrial production, where the adhesive is applied on the heated surface of a Yankee cylinder. The spray unit may be arranged on the side of the linear path of the sled or above the linear path of the sled. For example, the sled may pass under the spray nozzle of the spray unit, the spray nozzle applying the chemical to the test surface. According to one embodiment of the invention the arrangement can comprise a plurality of separate spray units, arranged along the linear path of the sled. The spray units may be operated individually or in communication which each other. Plurality of nozzles in one spray unit and/or plurality of spray units provide possibility to test even complex combinations of different chemicals.

The spray nozzle of the spray unit is any suitable liquid nozzle. Preferably the spray nozzle is replaceable. Change of spray nozzle provides for possibility to test easily different spray patterns and/or different flow rates, which increases the flexibility of the arrangement. The spray nozzle of the spray unit may be connected to a pressure tank, which comprises the chemical to be sprayed. The pressure tank may be connected to a compressed air system or inflated manually. Flow rate and/or feeding pressure of the chemical may be controlled and adjusted according to the need.

The creping unit comprises the creping blade, which is arranged to pass over the test surface when the sled passes the creping unit. The creping unit is situated after the spray unit and after the optional press unit. The creping blade is arranged to a blade holder and attached with suitable attachment means to the holder, for example with screws. The size of the creping blade may be selected according to suit the other measurements of the arrangement. The length of the creping blade may be, for example, 100-200 mm, preferably 110-150 mm, and the width of the creping blade may be, for example 80-120 mm, preferably 90-110 mm. The thickness of the creping blade may be at least 0.8 mm. Similarly the angle between the creping blade and the test surface may be adjusted according to the need. In this manner it is possible to test different creping blade compositions, grind angles and/or creping pocket angles, and their effect to the creping result.

At the creping unit the sled with the test surface passes underneath the creping blade of the creping unit. The creping blade comes into contact with the slightly sloping leading edge of the test surface, whereby the creping blade bends and creates a vertical load as the creping blade reaches the middle part of the test surface. When a test tissue sheet has been applied on the middle part of the test surface at the press unit, it has been dried to correct consistency, i.e. moisture content, when the test surface reaches the creping unit and the test tissue sheet is creped off the test surface by the creping blade. During the creping the creping blade is subjected to a horizontal creping force.

According to one preferred embodiment of the invention creping blade is arranged to exert a vertical load to the test surface when passing the test surface. The load force of the creping blade against the test surface may be adjusted by using load adjusting means, such as load adjustment screw(s). The creping unit may comprise or it may be in functional contact with measurement means, which measure data related to the force between the creping blade and the test surface. The measurement means may comprise a first load cell and a second load cell, which both are arranged into a functional contact with the creping blade; collection means for collecting and preserving the obtained data; and calculation means for calculating on basis of the obtained data the forces relevant in creping, such as orthogonal forces. According to one preferred embodiment of the invention the creping unit comprises preferably at least a first load cell for measuring the vertical load on the creping blade and a second load cell for measuring the horizontal load during the creping, i.e. for measuring the load in horizontal direction. The first and second load cells convert the load forces into electrical signals which are transmitted to the data collection means, where they are handled and stored. From the collected data final load force results may be calculated by using calculation means.

According to one advantageous embodiment of the present invention the arrangement comprises a press unit with a press roll, the press unit being arranged between the spray unit and the creping unit along the linear path of the sled and the press roll being arranged to pass over the test surface when the sled passes the press unit. The press roll is operated by press roll drive means, such as a servomotor or the like. The press roll is rotating at a suitable speed and pressed against the test surface when it passes the press unit. The press force of the press roll towards the test surface is preferably adjustable by using press force adjusting means, such as springs and/or force adjustment screw(s). The maximum pressing force between the press roll and the test surface may be selected depending on the overall arrangement configuration, but it may be, for example, 2000-10 000 N, preferably 6000-8000 N.

The press roll preferably comprises a felt, which is arranged around the press roll circumference. The felt may be attached by using suitable attachment means, such as clamping edge or the like. A test tissue sheet may be applied on the felt surface. When the test surface passes the press unit, the press roll is pressed against the test surface and the test tissue sheet is pressed against the test surface, on to which it adheres. According to the one preferred embodiment of the invention the test tissue sheet is applied onto the test surface after the spraying of the chemical, whereby the creping blade of the creping unit removes the test tissue sheet from the test surface while passing the surface. The test tissue sheet is transferred from the press roll of the press unit to the heated test surface by a combination of hydraulic forces and adhesive forces.

According to one preferred embodiment the felt may be wetted before application of the test tissue sheet. The pressing force of the press roll both dewaters the test tissue sheet and transfers the test tissue sheet from the wet felt to the heated test surface. For example, the press roll dewaters the test tissue sheet to consistency of 37-45%. A more accurate estimate about behavior of the tissue in real process conditions may thus be obtained.

According to one embodiment of the present invention the sled is accelerated to a predetermined second speed after the press unit and before the creping unit. The sled exits the pressure unit before it accelerates to the second speed, i.e. creping speed. The acceleration stage to the second speed ends before the creping unit such that the sled passes the creping unit at constant predetermined second speed. The test tissue sheet dryness and the film strength of the applied chemical may adjusted or corrected by adjusting and selecting the sled speed between the press unit and creping unit, which naturally determines the time lapsing between the two units as well as the performed operations. Typically the second speed is higher than the first speed, but is some embodiments the first speed and the second speed are substantially same, or in some embodiments the first speed may even be higher than the second speed. In this manner, the arrangement and the method provide extensive possibilities to test and simulate different process conditions, and to gain understanding of the creping process.

After the creping unit the sled is decelerated and stopped before reaching the second end of the guide rail.

The test tissue sheet may be freely chosen. By using the arrangement and the method according to the present invention it is easy to test tissue sheets with different consistency, density and/or fiber composition. Because the test procedure is simple and fast to perform, and the amount of tissue sheet and chemicals is small, there are few economical and/or time bound limitations for testing of different combinations. For example, test tissue sheet can be formed by using dynamic sheet former, which is capable of controlling sheet basis weight, MD/CD fiber orientation and uniformity. Typically the test tissue sheet, which is tested by using the arrangement described in this application, has not been fully dried before simulation testing. The test tissue sheet may be dewatered to a consistency of approximately 50%, before it is applied on the surface of the pressure roll. Thus the obtained results closely match the commercial operations.

According to one preferred embodiment the sled is arranged to travel along a linear horizontal guide rail. The guide rail has a first end and a second end, and its length may be freely selected, as long as the sled is able to reach the desired speed before the creping unit and decelerate before the second end of the guide rail. Typical length of the guide rail may be 3-10 meters, preferably 4-6 meters. The guide rail is preferably firmly supported and anchored to the ground by using any suitable supporting means and fastening means. The guide rail may be an aluminum profile. Preferably the guide rail comprises grooves and the sled comprises bearings, which are fitted to the grooves of the guide rail.

The drive and location devices of the arrangement generally comprise the drive means of the press roll and the sled, a timing belt with calibrated teeth as well as inductive sensors. Servomotors are preferred drive means because they enable accurate positioning of the sled along the guide rail and the rotational position of the press roll. The timing belt is also used for determining the accurate linear position of the sled along the guide rail. The location devices comprise also inductive sensors, positioned for example at the press unit and at the second end of the guide rail. The inductive sensors may be used to determine the position the sled and/or to confirm that the servomotor position calculations are correct.

According to one preferred embodiment of the present invention the arrangement is semi-automatic and can be operated by one process operator. Heating means, spray unit on/off, drive means of the press unit and the sled may be connected to and operated through an operator panel of central control means, such as personal computer. Spray pressure of the spray nozzle of the spray unit as well as pressing force of the press roll of the press unit and load of the creping blade are normally set manually. Also the application of the test tissue sheets on the press roll is done manually.

The invention is described in more detail below with reference to the enclosed schematic drawing, in which FIG. 1 shows an arrangement according to one embodiment of the invention, seen from side.

FIG. 1 shows an arrangement according to one embodiment of the invention, seen from side. The arrangement 1 comprises a sled 2 with a test surface 3, which can be heated to a desired test temperature. The sled 2 is transferred along a linear path with the aid of a timing belt 4, arranged around an idle roll 5 and a drive roll 5'. The sled 2 is shown in the zero position at the first end of the linear path. The dash line shapes 2', 2" represents the sled in various positions during the performance of the method.

At least on chemical is applied on the heated test surface 3 of the sled 2 by using a spray unit 6, which is represented by an arrow in FIG. 1. The sled 2 passes the spray unit 6, and the at least one chemical is sprayed from a spray nozzle (not shown) on the test surface 3.

After the spray unit 6 the sled 2 pass a press unit 7 which comprises a press roll 8. The press roll 8 rotates at the predetermined speed and is pressed against the test surface 3, when the sled 2 passes the press unit 7. The press force of the press roll 8 towards the test surface 3 is adjustable with press force adjusting means 9, such as adjustment screw(s) or spring(s). A test tissue sheet (not shown) is arranged on the surface of the press roll and pressed against the heated surface of the test surface 3.

The test tissue sheet is creped off from the test surface 3 at a creping unit 10. The creping unit 10 comprises a creping blade 101 as well as a first load cell 11 for measuring the vertical load on the creping blade 101 and a second load cell 12 for measuring the horizontal load during the creping.

The location device for determining the position of the sled 2 along the linear path comprises inductive sensors 13, 13' and a stopper 14 at the second end of the linear path.

It should be noted that the arrangements, its different units and individual parts and components are not presented in scale in FIG. 1. Some units, parts and components are presented off-scale, typically larger, in order to give a clear presentation.

Even if the invention was described with reference to what at present seems to be the most practical and preferred embodiments, it is appreciated that the invention shall not be limited to the embodiments described above, but the invention is intended to cover also different modifications and equivalent technical solutions within the scope of the enclosed claims.

The invention claimed is:

1. Arrangement for simulating creping of tissue, the arrangement comprising
    a sled with a test surface, which sled is arranged to travel along a linear path;

heating means for heating the test surface;
a spray unit with at least one spray nozzle, the spray unit being arranged along the linear path of the sled and the at least one spray nozzle being arranged to spray a chemical on the test surface;
a creping unit comprising a creping blade, the creping unit arranged along the linear path of the sled after the spray unit and the creping blade arranged to pass over the test surface when the sled passes the creping unit; and
measurement means for measuring data related to force between the creping blade and the test surface.

2. Arrangement according to claim 1, characterized in that the arrangement comprises a press unit with a press roll, the press unit being arranged between the spray unit and the creping unit along the linear path of the sled and the press roll being arranged to pass over the test surface when the sled passes the press unit.

3. Arrangement according to claim 1, characterized in that the measurement means comprises a first load cell and a second load cell, which both are arranged into a functional contact with the creping blade; collection means for collecting and preserving the obtained data, and calculation means for calculating on basis of the obtained data the force between the creping blade and the test surface.

4. Arrangement according to claim 1, characterized in that the sled is arranged to travel along a linear horizontal guide rail.

5. Arrangement according to claim 1, characterized in that the test surface is a part of a test plate, which is detachably arranged to the sled.

6. Arrangement according to claim 1, characterized in that the heating means comprises a heating element, which is arranged to the sled.

7. Arrangement according to claim 1, characterized in that the creping blade is arranged to exert a load to the test surface when passing the test surface.

* * * * *